(12) United States Patent
Murdeshwar et al.

(10) Patent No.: US 11,950,964 B2
(45) Date of Patent: Apr. 9, 2024

(54) MEDICAL DEVICE WITH MITIGATION FOR TISSUE PERFORATION

(71) Applicant: GYRUS ACMI, INC., Southborough, MA (US)

(72) Inventors: Nikhil M. Murdeshwar, Maple Grove, MN (US); Kester J. Batchelor, Mound, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 403 days.

(21) Appl. No.: 16/276,896

(22) Filed: Feb. 15, 2019

(65) Prior Publication Data

US 2020/0261178 A1 Aug. 20, 2020

(51) Int. Cl.
*A61B 90/00* (2016.01)
*A61B 18/00* (2006.01)
*A61B 34/20* (2016.01)
*A61B 17/00* (2006.01)

(52) U.S. Cl.
CPC .............. *A61B 90/06* (2016.02); *A61B 18/00* (2013.01); *A61B 34/20* (2016.02); *A61B 2017/00084* (2013.01); *A61B 2018/00559* (2013.01); *A61B 2018/00577* (2013.01); *A61B 2034/2046* (2016.02); *A61B 2090/065* (2016.02); *A61B 2090/08021* (2016.02)

(58) Field of Classification Search
CPC ....... A61B 5/065; A61B 5/6885; A61B 17/42; A61B 17/4241; A61B 2017/00022; A61B 2017/00026; A61B 2017/4216; A61B 2017/4225; A61B 2017/4233; A61B 2018/00559; A61B 90/06; A61B 2090/062; A61B 2090/064; A61B 2090/065; A61M 2205/332
See application file for complete search history.

(56) References Cited

U.S. PATENT DOCUMENTS

| | | | |
|---|---|---|---|
| 9,055,950 B2 | 6/2015 | Beani et al. |
| 9,993,290 B2 | 6/2018 | Chee et al. |
| 2003/0220636 A1 | 11/2003 | Bowman et al. |
| 2008/0154090 A1 | 6/2008 | Hashimshony |
| 2009/0259106 A1 | 10/2009 | Catapano et al. |
| 2010/0087798 A1 | 4/2010 | Adams et al. |
| 2010/0114083 A1 | 5/2010 | Sharma |
| 2012/0220879 A1 | 8/2012 | Fandrey et al. |

(Continued)

FOREIGN PATENT DOCUMENTS

| | | |
|---|---|---|
| CN | 111568532 A | 8/2020 |
| EP | 3695801 A1 | 8/2020 |

OTHER PUBLICATIONS

"European Application Serial No. 20157328.4, Extended European Search Report dated Jul. 13, 2020", 9 pgs.

(Continued)

*Primary Examiner* — Diane D Yabut
(74) *Attorney, Agent, or Firm* — Schwegman Lundberg & Woessner, P.A.

(57) ABSTRACT

A medical device that includes an introducer and a sensor. The introducer is configured to be inserted into a body cavity through a constricted channel. The introducer includes a predetermined section. The sensor is configured to generate a signal while the predetermined section of the introducer is located inside of the body cavity.

20 Claims, 8 Drawing Sheets

(56) References Cited

U.S. PATENT DOCUMENTS

| | | |
|---|---|---|
| 2014/0094649 A1 | 4/2014 | Ito |
| 2015/0223704 A1* | 8/2015 | Haverkost ............ A61B 5/6856 600/481 |
| 2015/0335380 A1 | 11/2015 | Chee et al. |
| 2017/0143410 A1 | 5/2017 | Truckai |
| 2017/0196478 A1 | 7/2017 | Hunter |
| 2018/0055478 A1 | 3/2018 | Choi et al. |
| 2019/0223759 A1* | 7/2019 | Page ...................... A61B 34/32 |

OTHER PUBLICATIONS

"European Application Serial No. 20157328.4, Response filed Feb. 17, 2021 to Extended European Search Report dated Jul. 13, 2020", 10pgs.

"Chinese Application Serial No. 202010097243.7, Office Action dated Aug. 17, 2023", w/ English Translation, 18 pgs.

* cited by examiner

MEDICAL DEVICE WITH MITIGATION FOR TISSUE PERFORATION

FIELD

These teachings relate to a medical device and method for treating body tissue.

BACKGROUND

Menorrhagia is a medical condition that includes abnormally heavy and prolonged menstrual bleeding and pain. For decades, hormone pills and/or hysterectomy were used to treat menorrhagia.

Recently, medical devices have been introduced to treat menorrhagia by way of endometrium ablation, where the endometrium is exposed to various treatment modalities such as RF energy, cryogenics, thermal energy, microwave energy, and/or steam.

While often effective, many of the available medical devices suffer from one or more challenges or deficiencies.

For example, during insertion of the medical device into the uterus and/or maneuvering or manipulation of the device inside of the uterus, there is a risk of tissue perforation, which may cause patent trauma and discomfort and/or may undesirably prolong a medical procedure. Moreover, if the medical device is not property implanted, positioned, or aligned inside of the uterus before or during treatment, the efficacy of the treatment may be impacted.

Some available medical devices are configured for blind insertion into the uterus. Once inside, one or more devices are configured to project or extend from a distal portion of the medical device to contact tissue inside of the uterus to verify measurements and/or a position of the medical device inside of the uterus. Extending or projecting such measurement devices inside of the uterus may undesirably scrape or perforate tissue inside the uterus, which may cause patient trauma and discomfort and/or prolong a medical procedure. Some examples of medical devices are disclosed in U.S. Pat. No. 9,055,950 and US 20170143410A1, which are incorporated by reference herein for all purposes.

In view of at least the aforementioned, improvement in the art may be desirable.

For example, it may be desirable to have a medical device and method that mitigates tissue perforation during implantation of the medical device into the uterus. It may be desirable to have a medical device and method configured to alert a user when or after a predetermined section of the medical device has been inserted into a body cavity, like a uterus, and/or is no longer located inside of a body lumen or constricted channel, like a uterine os, cervix, or vagina.

It may be desirable to have a medical device that is configured to provide an alert or notification when or after a predetermined section of the medical device has entered a body cavity and/or is no longer located within a body lumen, without using devices that are configured to project or extend out of the medical device after a portion of the medical device is located inside of the body cavity.

SUMMARY

A medical device and method is disclosed. The medical device includes features for mitigation of tissue perforation. The method includes steps for mitigation of tissue perforation during insertion of a medical device into a body cavity. The medical device is configured to provide an alert or notification when or after a predetermined section of the medical device has entered a body cavity, like a uterus, and/or is no longer located inside of any body lumen, like a uterine os. Advantageously, by utilizing the device and method teachings herein, a user will no longer have to rely on feeler or other measurement tools to contact tissue inside of the body cavity to determine device placement inside of the body cavity, thus mitigating risk of tissue perforation inside of the body cavity.

These teachings provide a medical device that is configured to provide a signal after a predetermined section of the medical device is located inside of a body cavity, without requiring hysteroscopy. Advantageously, by not requiring hysteroscopy, time required for a medical procedure may be shortened and/or less tools are required at the surgical site, which may reduce clutter/obstructions and/or reduce overall costs of the medical procedure.

Moreover, by understanding when or after a predetermined section of the medical device is located inside of a body cavity, there may be a reduction in device manipulation and/or maneuvering inside the anatomy, which may advantageously reduce chances of tissue perforation.

A medical device comprising an introducer and a sensor. The introducer is configured to be inserted into a body cavity through a constricted channel. The introducer comprises a predetermined section. The sensor is configured to generate a signal while the predetermined section of the introducer is located inside of the body cavity.

A medical device comprising and introducer and a sensor. The introducer is configured to be inserted into a body cavity through a body lumen. The introducer is configured to place the sensor in intimate contact with tissue during insertion of the introducer into the body lumen and to remove the sensor from the intimate contact with tissue after the introducer is inserted into the body cavity. The sensor is configured to provide a first signal when the sensor is in intimate contact with the tissue and to provide a second signal when the sensor is free of the intimate contact with the tissue.

DETAILED DESCRIPTION

Figure 1:
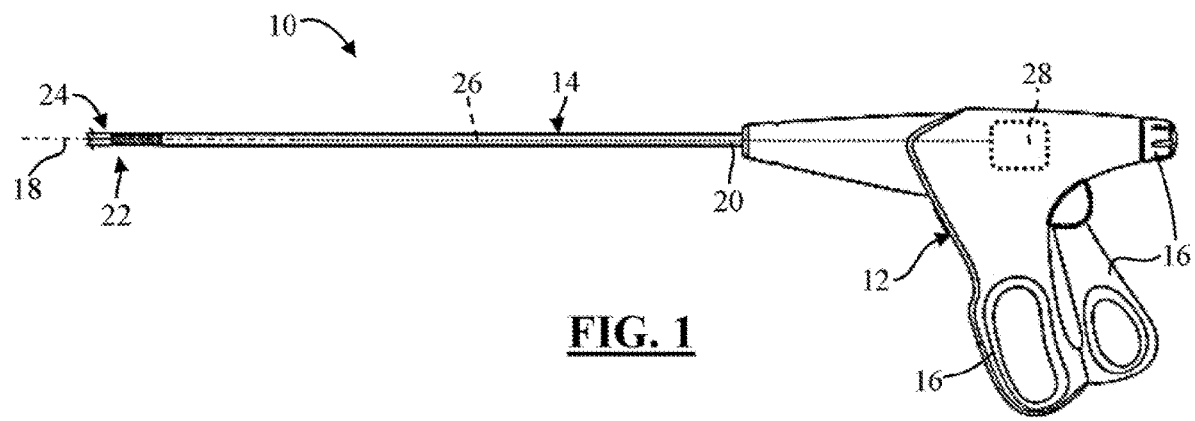
FIG. 1 is a side view of a medical device.

These teachings provide a medical device and method. The medical device and method may be used to treat or effect an anatomical feature. The anatomical feature may be any anatomical feature, such as a body cavity or a body lumen. The medical device may be configured to treat menorrhagia. The medical device may be configured to effect or destroy the endometrium.

While the medical device disclosed herein may be used to treat menorrhagia, it is understood that the medical device can be used in other applications as well. For example, the device and system can be used to treat tissue in the bladder, vagina, esophagus, trachea, urethra, ureter, prostate gland, kidney, intestinal growths or abnormal tissues of the intestine, cancerous tissue, etc.

The medical device may comprise a hand piece. The hand piece may function to be held by a user or robot and/or support or contain one or more components of the medical device. For example, the hand piece may support or contain one or more elements or devices for treating the anatomy. The hand piece may contain one or more communication devices and/or the controller. The hand piece may comprise a one or more indicators that can be used by the sensor(s) and/or controller according to these teachings to communicate with a user and/or robot and/or controller. For example, the one or more indicators may include one or more lights, speakers, a display such as an LCD, or a combination thereof. For example, the one or more indicators may be used to communicate to a user or computer when the predetermined section of the introducer and/or medical device is within a body lumen; is within a body cavity; is partially within the body lumen and/or body cavity; or a combination thereof.

The medical device and/or the hand piece may comprise one or more user controls. Movement or manipulation of the one or more user controls may function to move or actuate the introducer; activate or de-activate one or more treatment modalities for treating the anatomy before during or after the introducer or predetermined section is located inside of the body lumen and/or body cavity; extend or retract one or more anatomical treatment elements, like an ablation mechanism, electrode array, balloon, etc. The one or more user controls may be one or more switches, levers, buttons, triggers, knobs, rotation wheels, or a combination thereof. The one or more user controls may also be a foot pedal in communication with the medical device.

The medical device comprises an introducer. The introducer may function to permit a portion of the medical device to be inserted into a patient or the anatomy, while a portion of the device remains outside of the patient or anatomy. The introducer may be configured to place the one or more sensors in intimate contact with tissue defining a body lumen or constricted channel during insertion of the introducer into the body lumen. The introducer may be configured to remove the one or more sensors from intimate contact with tissue of the body lumen after the introducer is inserted into the body cavity or the introducer is withdrawn from the body lumen.

The introducer may be a tubular member. The introducer may be a braided or coiled tube. The introducer may be a tube that is generally smooth on the inside and outside surfaces. The introducer may be an elongated member that extends along a longitudinal axis. The proximal end or proximal portion of the introducer may be connected to the hand piece. The distal end or the distal portion of the introducer may define a mouth or opening through which one or more treatment devices may be located, such as a balloon, a beam disperser, electrode array. The introducer may have a relatively small diameter, on the order of about 10 mm or less, 9 mm or less, 8 mm or less, 7 mm or less, or even 6 mm or less. The diameter of the introducer may be less than 6 mm. Such relatively small sized introducer may be advantageous in minimizing patient trauma during insertion and/or removal of the introducer into and from a body lumen and/or body cavity.

The introducer may be substantially straight and/or may include sections that are substantially straight; may include one or more angles, bends or arcs and/or may include sections that have one or more angles, bends or arcs; or a combination thereof. The introducer may be substantially rigid, substantially flexible, substantially resilient, substantially kink-resistant, or a combination thereof. The introducer may be configured in such a way to allow angular movements and/or can be advanced along a tortuous path within a body lumen and/or body cavity.

The medical device and/or the introducer may comprise one or more predetermined sections. A predetermined section may be any part of the introducer. A predetermined section of the introducer may be any section(s) or portion(s) of the introducer that a user is interested in knowing its relative position inside of the anatomy, such as inside of a body lumen and/or inside of a body cavity. The predetermined section may be located at a distal end of the introducer. The predetermined section may include the distal-most end of the introducer. The predetermined section may be a section of the introducer that is located proximal of the distal-most end of the introducer.

The predetermined section may be an area of the introducer that includes one or more treatment modalities or elements for treating a body cavity and/or body lumen. For example, the predetermined section may include one or more ports, orifices, nozzles, and/or any other suitable dispensing features for delivering one or more treatment fluids of elements into the anatomy. The predetermined section may be a section or area of the introducer or medical device where one or more treatment elements like one or more balloons and/or electrodes are located or configured to extend from the medical device.

The predetermined section may have a length that is approximately 1.0 cm. The predetermined section may have a length that is 0.2 cm or more, 0.3 cm or more, 0.4 cm or more, 0.5 cm or more, 0.8 cm or more, 1.0 cm or more, 1.2 cm or more, 1.5 cm or more, 1.8 cm or more, 2.0 cm or more.

The predetermined section may be contoured or tapered to assist in inserting the introducer and/or medical device into the anatomy.

The medical device may comprise one or more sensors. The one or more sensors may be used to determine a relative position of the introducer relative to the anatomy, a body cavity, a body lumen or constricted channel, the ground (i.e., earth), a site or feature of interest, any known or home position, or a combination thereof. The one or more sensors may be used to determine when a predetermined section of the introducer is located outside of a body lumen, located outside of the body cavity, located inside of a body lumen, located inside of a body cavity, or a combination thereof.

The one or more sensors may be configured to generate one or more electrical signals relating to a position or location of the introducer and/or a position or location of the predetermined section of the introducer.

The one or more sensors may be configured to communicate the one or more generated electrical signals to a user and/or controller for determining, calculating, and/or translating the one or more generated signals to a relative position of the introducer or the predetermined section relative to the anatomy, a body cavity, a body lumen, the ground, a site or feature of interest, a known position, or a combination thereof.

One or more of the sensors may be located on an outer surface of the introducer. One or more of the sensors may be located at least partially within or embedded in an outer surface of the introducer. The one or more sensors may be proud of an outer surface of the introducer, flush with an outer surface of the introducer, or sub flush with an outer surface of the introducer.

One or more of the sensors may be located within the predetermined section of the introducer. One or more of the sensors may be located proximal of the predetermined section of the introducer. One or more of the sensors may be located distal of the predetermined section of the introducer.

The one or more sensors may be any sensor that is configured to generate a signal when the sensor is in contact with tissue anatomy. The one or more sensors may be a mechanical sensor. A mechanical sensor may be a contact sensor. The sensor may be displaced, translated, compressed, deformed, depressed, biased, rotated (clockwise or counter clockwise) and/or otherwise moved relative to the introducer or hand piece by a force. The force may be provided by the tissue or anatomical feature defining the body lumen or constricted channel. The force may be a result of the size of the introducer and/or sensors being slightly larger than a size or diameter of the opening in the constricted channel. The force may be a result of the one or more sensors being in contact, or in intimate contact, or in direct contact, with tissue or anatomy defining the body lumen or constricted channel.

After a portion of the mechanical sensor is compressed, deformed, depressed, translated, and/or otherwise moved by tissue and/or anatomical while the sensor is inside a body lumen, an electrical circuit may be opened or closed, which may cause the one or more sensors to generate one or more signals indicative of the sensor being in a particular location (i.e., within a body lumen) and then transmit the signal to a controller for calculating and/or displaying to a user.

A portion of the mechanical sensor may be uncompressed, undeformed, undepressed, while the sensor is outside of a body lumen or inside of a body cavity. An uncompressed sensor may be its steady state position.

After a portion of the mechanical sensor is uncompressed, undeformed, undepressed, and/or otherwise moved into a steady state position an electrical circuit may be opened or closed, which may cause the one or more sensors to generate one or more signals indicative of the sensor being in a particular location (i.e., outside of a body lumen or inside of a body cavity) and then transmit the signal to a controller for calculating and/or displaying to a user.

The one or more sensors may be a temperature sensor. For example, the temperature of the tissue or anatomy may be different between a body lumen or constricted channel and a body cavity, and the sensor may be able to detect a change in the temperature of the tissue or anatomy. For example, when the predetermined section is located inside of the constricted channel or body lumen, the tissue defining the constricted channel may be in contact with the sensor, and the sensor can measure a temperature of the tissue. In contrast, when the predetermined section is located inside the body cavity, the sensor is free of contact with any tissue but is instead in contact with surrounding fluid. The surrounding fluid may have a different or reduced temperature compared to the temperature of the tissue. Accordingly, the differences in temperature can be used by the sensor to determine if the predetermined section is located inside of the constricted channel or body cavity.

The one or more sensors may be electrical terminals. When tissue or an anatomical feature is in contact with two or more sensors, an electrical circuit may be closed or completed through the conductive tissue. The closed or completed circuit may function to generate a signal that is indicative of the sensors being in contact with tissue, which is indicative of the predetermined section and/or sensors being in a particular location, like a constricted channel or body lumen.

The sensor may comprise one or more sensors. For example, a sensor may comprise a first sensor, a second sensor, a third sensor, and so on. For example, a sensor may comprise a proximal sensor, a distal sensor, a lateral sensor, etc. The sensor is configured to provide a signal (e.g., a first signal) after the distally-located contact sensor is in the intimate contact with the tissue and the proximally-located contact sensor is in the intimate contact with the tissue. The first signal may be indicative of the predetermined section being located inside of the constricted channel.

The sensor may be configured to provide a signal (e.g., a second signal) after the distally-located contact sensor is free of the intimate contact with the tissue and the proximally-located contact sensor is free of the intimate contact with the tissue. The second signal may be indicative of the predetermined section being located inside of the body cavity, or located outside of the constricted section.

The medical device may include one or more controllers. The controller may be or include a processor; memory; stored data (i.e., equations and/or lookup table); a signal emitting device, such as one or more lights, one or more speakers, a display such as LCD; or a combination thereof. The controller may be part of one or more of the sensors. The controller may be located in the hand piece, introducer, medical device. The controller may be located away from the medical device, for example at a remote location or computer.

The controller may function to receive one or more signals from the sensor. The controller may function to process one or more signals from the sensor. The controller may function to translate or correlate, via the stored data—equations and/or lookup table, the one or more signals received from the sensor to a relative position of the introducer and/or the predetermined section of the introducer relative to a body lumen and/or body cavity.

For example, based on one or more signals received from the sensor, the controller may function to correlate or calculate or determine whether the predetermined section of the introducer is located outside of a body lumen, located outside of the body cavity, located inside of a body lumen, located inside of a body cavity, or a combination thereof.

The controller may function to alert, notify, and/or communicate a signal and/or the relative position of the introducer and/or the predetermined section of the introducer relative to a body lumen and/or body cavity to a user or computer. The signal may be communicated to a user via one or more lights (i.e., flashing lights, illuminated lights, lights turned OFF, lights changing colors, etc.); one or more speakers (i.e., an audible tone or a change in one); one or more tactical features like a vibration or pulse; an image or light displaced on a display like an LCD, or a combination thereof.

The one or more signals communicated from the sensor to the controller and/or from the controller to a user or computer may be a DC signal, an AC signal, a low voltage signal, or a combination thereof.

The controller may be connected to the one or more sensors via one or more communication devices. The communication device may function to send, communicate, and/or transmit one or more signals from or between the one or more sensors and the controller. The one or more communication devices may include: one or more electrical wires; one or more wireless communication devices like Bluetooth, radio waves, wireless LAN, WIFI, cellular networks, etc.

FIG. 1 illustrates a medical device 10. The medical device 10 comprises a hand piece 12 and an introducer 14. The hand piece 12 is configured to be gripped or held by a user. The hand piece 12 comprises one or more user controls 16 for operating, manipulating, and/or otherwise using the medical device 10. The introducer 14 extends along a longitudinal axis 18, between a proximal portion 20 that is connected to the hand piece 12 and a distal portion 22 that is located opposite the proximal portion 20.

The medical device 10 comprises a sensor 24. The medical device 10 comprises one or more communication devices 26 electrically connecting the sensor 24 and a controller 28 for communicating signals between the sensor 24 and the controller 28. The controller 28 may be located inside of the medical device 10 and/or the hand piece 12, or the controller 28 may be located at a remote location away from the medical device 10. In some configurations, the controller 28 may be part of or incorporated into or with the sensor 24.

Figure 2:
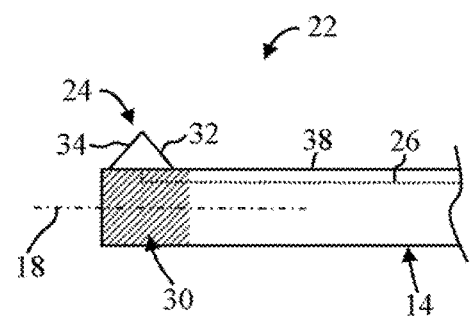
FIG. 2 is a side view of a distal portion of the medical device of FIG. 1.

FIG. 2 illustrates the distal portion 22 of the introducer 14. The introducer 14 comprises a predetermined section 30. The sensor 24 (i.e., one or both faces 32, 34 discussed below) may be located within the predetermined section 30; may be located distal of the predetermined section 30; may be located proximal of the predetermined section 30, or a combination thereof.

The sensor 24 includes a proximal face 32 and a distal face 34. The proximal face 32 is canted and extends in a distal direction and at an angle relative to the longitudinal axis 18 and/or an outer surface 38 of the introducer 14. The distal face 34 that is canted and extends in a proximal direction and at an angle relative to the longitudinal axis 18 and/or outer surface 38 of the introducer 14. In some configurations, one or both of these faces 32, 34 may be generally perpendicular to the longitudinal axis 18 and/or outer surface 38 of the introducer 14. In some configurations, one or both of the faces 32, 34 may be canted in an opposite direction; that is, face 32 may be canted in a proximal direction and face 34 canted in a distal direction.

Figure 3A:
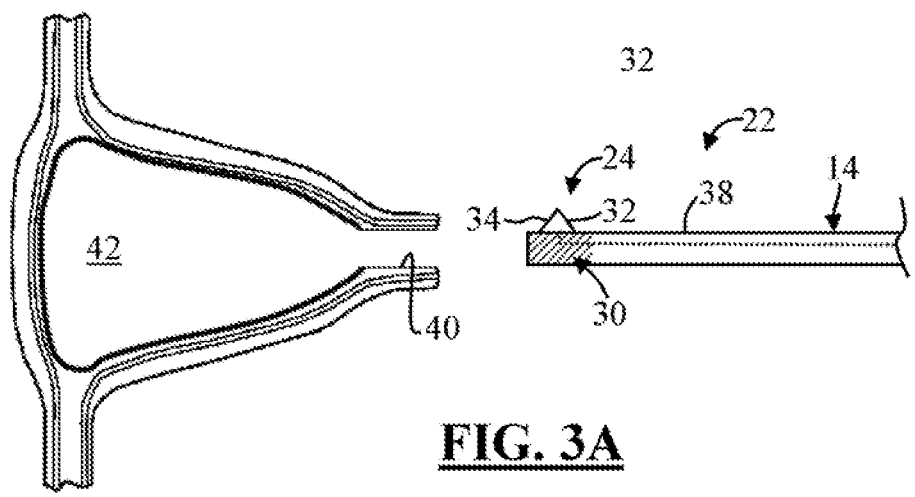
FIGS. 3A-3C are side views of the distal portion of the medical device of FIG. 2 being inserted into a body cavity through a constricted channel.

FIG. 3A illustrates the distal portion 22 of the introducer 14 positioned outside of or away from a body lumen or constricted channel 40 that leads into a body cavity 42. In this example, the constricted channel 40 is a cervical canal or os, and the body cavity 42 is a uterus. However, the constricted channel or body lumen 40 can be any constricted channel or body lumen, and the body cavity 42 can be any body cavity or opening. Constricted channel 40 and body lumen may be used interchangeably in any of the examples discussed herein.

The sensor 24 may be a mechanical contact sensor. Before the distal portion 22 of the introducer 14 is inserted into the constricted channel 40, little or no force is acting on the sensor 24. Before the distal portion 22 of the introducer 14 is inserted into the constricted channel 40, the sensor 24 is free of any intimate contact with tissue defining the constricted channel 40. Accordingly, the proximal and distal faces 32, 34 remain in a steady state position, which is a position where the sensor 24 and/or one or both of the faces 32, 34 are spaced apart or elevated from an outer surface 38 of the introducer 14. The sensor 24 or one or both of the faces 32, 34 may be biased into the steady state or elevated position illustrated in FIG. 3A by way of a biasing member or spring (i.e., element 50 in FIG. 8, for example) and/or by way of one or both of the faces 32, 34 being constructed of a resiliently bendable material that is configured to move into the steady state or elevated position when little or no force is acting on the sensor 24 or one or both faces 32, 34.

When the sensor 24 is in a steady state position or is spaced apart from the introducer 14, the sensor 24 may be configured to generate and/or communicate one or more corresponding signals to the controller 28 (FIG. 1). The sensor 24 and/or the controller 28 may be configured to correlate or determine from the communicated signal(s) that the predetermined section 30 of the introducer 14 is not located inside of the constricted channel 40 and/or that the predetermined section 30 is located outside of the constricted channel 40. The controller 28 may communicate this signal or one or more other signals to a user, computer, or other controller to alert or notify the user or computer that the predetermined section 30 of the introducer 14 is not positioned inside the constricted channel 40. (in combination with other cues the operator can determine that this means the predetermined section of the introducer is located outside of the body lumen 40.)

For example, when the sensor 24 is spaced apart from the introducer 14, an electrical contact or circuit may be broken or interrupted. The controller 28 may be configured to correlate the broken or open electrical connection or circuit to little or no tissue or other anatomy defining the constricted channel 40 pressing one or both of the faces 32,34 or sensor 24 in a direction towards the outer surface 38 of the introducer 14 which means that the predetermined section 30 of the introducer 14 is not located within the constricted channel 40.

Figure 3B:
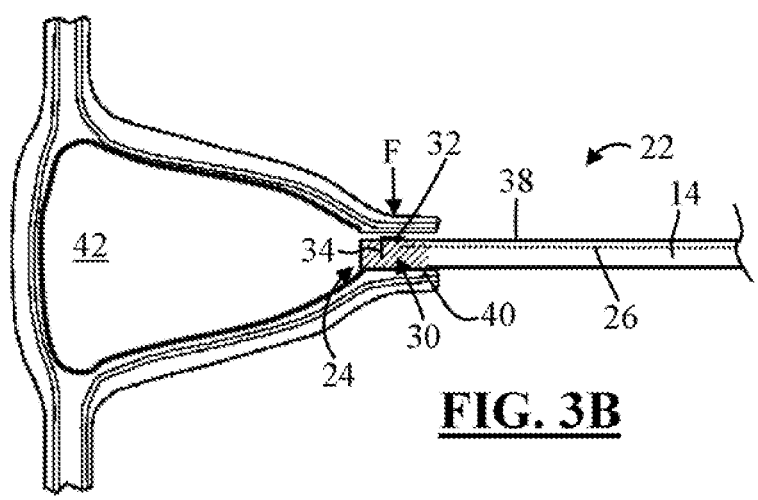

FIG. 3B illustrates the distal portion 22 of the introducer 14 located at least partially inside of the constricted channel 40.

A size or diameter of the introducer 14 is generally the same size or larger than a size or diameter of the constricted channel 40. Accordingly, when the distal portion 22 of the introducer 14 is moved into the constricted channel 40, the introducer 14 fits snuggly inside the constricted channel 40 and/or slightly expands the constricted channel 40. Due to the interference between the tissue or anatomy defining the constricted channel 40 and the introducer 14, and/or due to intimate contact between the tissue of the constricted channel 40 and the sensor 24, a force F is applied by the tissue or anatomy of the constricted channel 40 onto the sensor 24 and/or the distal face 32, which causes the sensor 24 and the faces 32, 34 to move or pivot or rotate into a compressed position. The sensor 24 is configured to rotate in a counterclockwise direction into the compressed position, as shown in FIG. 3B. That is, an end of the proximal face 34 may be pinned to the introducer 14 so that the distal face 34 and the proximal face 32 rotates down towards or into the outer surface 38 of the introducer 14.

During movement of the faces 32, 34 or the sensor 24 into the compressed position towards the outer surface 38 of the introducer 14, or after the faces 32, 34 or the sensor 24 is moved into close contact or into actual contact with the introducer 14, the sensor 24 may be configured to generate and/or communicate one or more corresponding signals to the controller 28 via the communication device 26. The controller 28 may be configured to correlate or determine from the communicated signal(s) that the predetermined section 30 of the introducer 14 is located inside of the constricted channel 40; and/or that the predetermined section 30 of the introducer 14 is no longer located outside of the constricted channel 40; and/or that the predetermined section of the introducer 14 is not located inside of the body cavity 42. The sensor 24 and/or controller 28 may communicate one or more corresponding signals to a user or computer to alert the user or computer that the predetermined section 30 is located inside of the constricted channel 40; and/or that the predetermined section 30 of the introducer 14 is no longer located outside of the constricted channel 40; and/or that the predetermined section of the introducer 14 is not located inside of the body cavity 42.

Figure 3C:
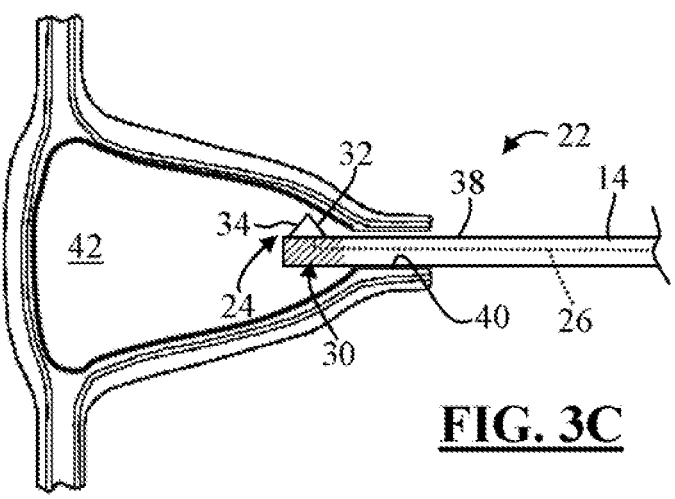

FIG. 3C illustrates the predetermined section 30 of the introducer 14 located inside of the body cavity 42.

When or after the predetermined section 30 of the introducer 14 is positioned inside of the body cavity 42, reduced or no force from tissue or other anatomical features defining the constricted channel 40 is applied on the sensor 24, the proximal face 32, and/or distal face 34 of the sensor 24. When or after the predetermined section 30 of the introducer 14 is positioned inside of the body cavity 42, the sensor 24 and/or the faces 32, 34 are free of intimate contact with the tissue of the constricted channel 40. Accordingly, the faces 32, 34 and/or the sensor 24 moves away from the outer surface 38 of the introducer 14 and into the steady state uncompressed position.

When the faces 32, 34 or sensor 24 is spaced apart from the introducer 14, the controller 28 may be configured to correlate or determine the predetermined section 30 of the introducer 14 is located outside of the constricted channel 40 (or is not located inside of the constricted channel 40); and/or that the predetermined section 30 of the introducer 14 is located inside of the body cavity 42. The sensor 24 and/or controller 28 may communicate this signal or one or more other signals to a user, computer, or other controller to alert or notify the user or computer that the predetermined section 30 of the introducer 14 is located outside of the constricted channel 40; and/or that the predetermined section 30 of the introducer 14 is not located inside of the constricted channel 40; and/or that the predetermined section 30 of the introducer 14 is located inside of the body cavity 42.

The sensor 24 and/or controller 28 may be configured to differentiate between the position of the introducer 14 in FIG. 3A, where the predetermined section 30 is located outside of the body cavity 42 from the position of the introducer 14 in FIG. 3C, where the predetermined section 30 is located inside of the body cavity 42. In both of these positions, the sensor 24 and/or faces 32, 34 are spaced apart from the outer surface 38 of the introducer 14 and in an uncompressed position.

For example, the sensor 24 and/or controller 28 may be configured to differentiate between the two aforementioned positions by recognizing or recording an initial position of the sensor 24 or faces 32, 34 being spaced apart from the introducer 14 (FIG. 3A) in an uncompressed position, followed by the sensor 24 or faces 32, 34 being moved towards or into contact with the introducer 14 (FIG. 3B) into a compressed position, followed by movement of the sensor 24 or faces 32, 34 back away from the introducer 14 (FIG. 3C) into the uncompressed position. That is, a particular sequence of signals including a signal corresponding to the sensor 24 or faces 32, 34 being uncompressed that is proceeded by a signal corresponding to the sensor 24 or faces 32, 34 being compressed, may be indicative of the predetermined section 30 being located within the body cavity 42 as opposed to being located outside of the body cavity 42.

After the one or more signals are sent to the user or computer indicative of the predetermined section 30 of the medical device being located inside the body cavity 42, the user may recognize, conclude, determine, or understand that the medical device 10 is inside the body cavity 42, without using other additional or ancillary tools or sensors to feel or contact tissue inside of the body cavity 42 to determine device placement or position, which may undesirably perforate or scrape the tissue and/or add additional time to the medical procedure. After the one or more signals are sent to the user or computer indicative of the predetermined section 30 of the medical device being located inside the body cavity 42, one or more treatment modalities may be applied to the body cavity 42 and/or tissue or anatomical features within the body cavity 42.

Referring back to FIG. 3B, when the introducer 14 is then withdrawn from the cavity 42 and located within the constricted channel 40 again, the interference or intimate contact between the introducer 14 and the anatomy defining the constricted channel 14 causes a force F to be applied onto the sensor 24 and/or the sensor faces 32, 34. Because the proximal face 32 is pinned to the introducer 14, the force F causes the sensor 24 and faces 32, 34 to move or pivot or rotate from the position illustrated in FIG. 3C to the position illustrated in FIG. 3B, in a counter-clockwise direction as shown in FIG. 3B. That is, the proximal face 32 rotates down towards the outer surface 38 of the introducer 14. During the movement of the faces 32, 34 or the sensor 24, or after the face 32 or the sensor 24 is moved into close contact or into actual contact with the introducer 14, the sensor 24 may be configured to generate and/or communicate one or more corresponding signals to the controller 28 via the communication device 26. The controller 28 may be configured to correlate or determine from the communicated signal(s) that the predetermined section 30 of the introducer 14 is located inside of the constricted channel 40; and/or that the predetermined section 30 of the introducer 14 is no longer located outside of the constricted channel 40; and/or that the predetermined section of the introducer 14 is not located inside of the channel body cavity 42. The sensor 24 and/or controller 28 may communicate one or more corresponding signals to a user or computer to alert the user or computer that the predetermined section 30 is located inside of the constricted channel 40; and/or that the predetermined section 30 is no longer located outside of the constricted channel 40; and/or that the predetermined section is not located inside of the body cavity 42.

Figure 4:
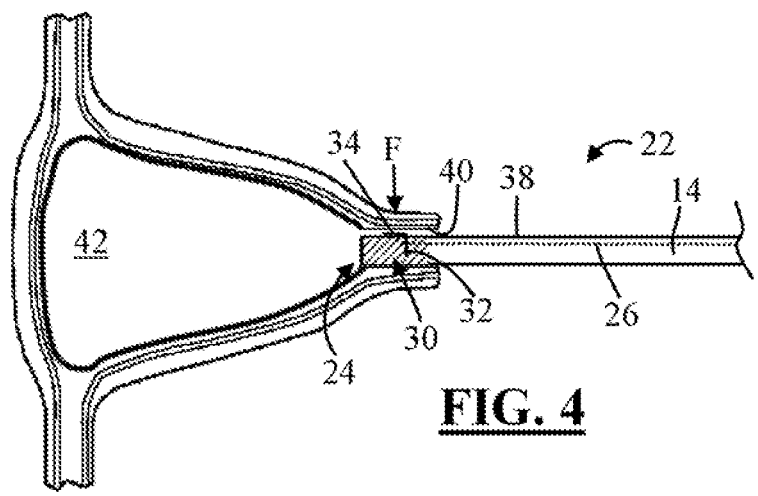
FIG. 4 is a side view of a distal portion of the medical device of FIG. 1 positioned inside of a constricted channel.

FIG. 4 illustrates a distal portion 22 of the introducer 14 that is substantially the same as the introducer illustrated and described in FIGS. 2-3C, except that distal face 34 of the sensor 24 is pinned to the introducer 14. This means that when the predetermined section 30 of the introducer 14 is inside of the constricted channel 40, an intimate contact or force D is applied by the tissue defining the constricted channel 40 onto the sensor 24, which causes the sensor 24 and the face 32, 34 to rotate in a clockwise direction such that the arm 34 is moved towards or into contact with the outer surface 38 of the introducer.

Figure 5:
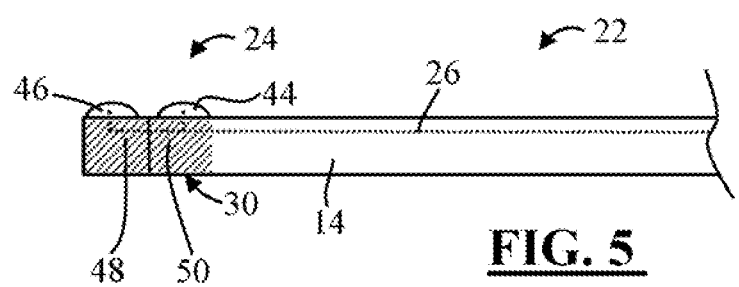
FIG. 5 is a side view of a distal portion of the medical device of FIG. 1

FIG. 5 illustrates the distal portion 22 of the introducer 14. The distal portion 22 of the introducer 14 comprises a predetermined section 30. The predetermined section 30 comprises a distal portion 48 and a proximal portion 50.

The sensor 24 comprises a proximally-located sensor 44 and a distally-located sensor 46. One or both of the sensors 44, 46 may be located within the predetermined section 30. Sensor 44 may be located within the proximal portion 50 of the predetermined section 30, and sensor 46 may be located within the distal portion 48 of the predetermined section 30.

In some configurations, the distally-located sensor 46 may be located distal of a distal-most end of the predetermined section 30 and/or distal of the distal-most end of the distal portion 48. Additionally, or alternatively, in some configurations, the proximally-located sensor 44 may be located proximal of a proximal-most end of the predetermined section 30 and/or proximal of the proximal-most end of the proximal portion 50.

One or more communication devices 26 are configured to electrically connect the sensors 44, 46 or sensor 24 and a controller 28 (FIG. 1). In some configurations, the function of the controller 28 may be combined or integrated with the sensor 24.

Figure 6A:
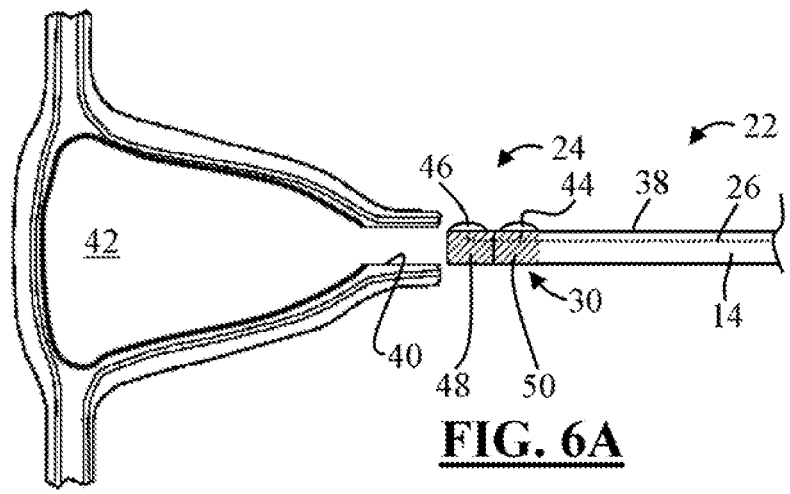
FIGS. 6A-6E are side views of the distal portion of the medical device of FIG. 5 being inserted into a body cavity through a constricted channel.

FIG. 6A illustrates the distal portion 22 of the introducer 14. The predetermined section 30 of the introducer 14 is located outside or away from a body lumen or constricted channel 40 that leads to a body cavity 42.

Before the distal portion 22 of the introducer 14 is inserted into the body lumen 40, the sensor 24 is free of intimate contact with the tissue of the constricted channel 40 or body lumen and, therefore, little or no force is applied on the sensor 24 and/or on both of the sensors 44, 46. Accordingly, both of the sensors 44, 46 or sensor 24 is/are elevated or spaced apart from the outer surface 38 of the introducer 14. The sensors 44, 46 or sensor 24 may be elevated or spaced apart from the outer surface 38 of the introducer 14 by way of a biasing member or spring and/or the sensors 44, 46 may be constructed from a resilient material that moves into a spaced apart relationship relative to the introducer 14 when little or no force is acting on the sensors.

When both of the sensors 44, 46 and/or the sensor 24 are elevated or spaced apart from the outer surface 38 of the introducer 14, the sensor 24 may be configured to generate and/or communicate one or more corresponding signals to the controller 28 (FIG. 1). The sensor 24 and/or controller 28 may be configured to correlate or determine from the communicated signal(s) that the predetermined section 30 of the introducer 14 is located outside of the constricted channel 40. The sensor 24 and/or controller 28 may communicate this signal or one or more other signals to a user, computer, or other controller to alert or notify the user or computer that the predetermined section 30 of the introducer 14 is located outside of the constricted channel 40.

For example, when both of the sensors 44, 46 are spaced apart from the outer surface 38 of the introducer 14, an electrical contact or circuit located between the sensors 44, 46; located between the sensors 44, 46 and the introducer 14; and/or located between the sensors 44, 46 and the communication device 26 may be broken or interrupted, which may be communicated via the communication device 26 to the controller 28. The controller 28 may be configured to correlate the broken or open electrical connection or circuit to little or no tissue or other anatomy defining the constricted channel 40 pressing the sensors 44, 46 down towards an outer surface 38 of the introducer 14 which means that the predetermined section 30 of the introducer 14 is located outside of, or not located within, the constricted channel 40.

Figure 6B:
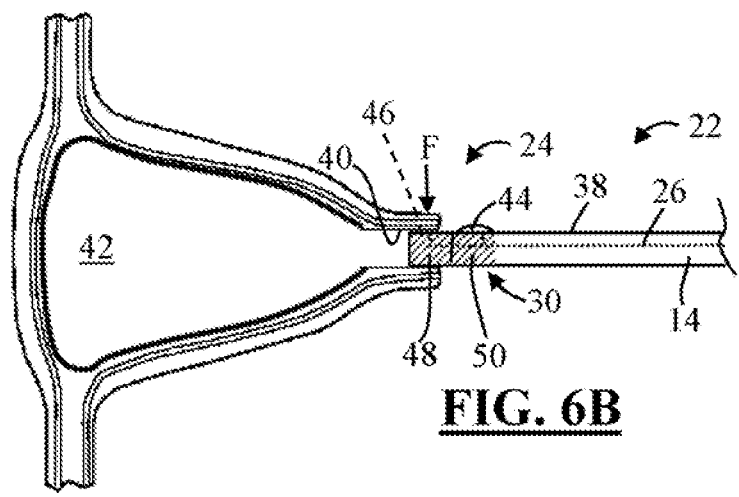

FIG. 6B illustrates the distal portion 22 of the introducer 14 at least partially inserted into the constricted channel 40. More specifically, the distal portion 48 of the predetermined section 30 is inserted into the constricted channel 40, while the proximal portion 50 remains outside of the constricted channel 40.

Because the introducer 14 is the same size or slightly larger than the constricted channel 40, when or after the distal portion 48 of the predetermined section 30 is inserted into the constricted channel 40, a force F is applied onto the distally-located sensor 46 due to the intimate contact between the sensor 46 and the tissue defining the constricted channel 40, which causes the distally-located sensor 46 to compress, move, or be biased towards the outer surface 38 of the introducer 14.

However, because the distal portion 22 of the introducer 14 has not been moved far enough into the constricted channel 42 for a force to be applied onto the proximally-located sensor 44, the proximally-located sensor 44 is free of any intimate contact with tissue and is therefore not compressed, or deflected, or moved or biased towards the outer surface 38 of the introducer 14. Instead, the proximally-located sensor 44 remains uncompressed, elevated, or spaced apart from the outer surface 38 of the introducer 14.

When or after the distally-located sensor 46 is compressed or moved towards the outer surface 38 of the introducer 14, an electrical contact or circuit may be completed, which the sensor 24 or controller 28 (FIG. 1) may correlate to the distal portion 48 of the predetermined section 30 being located inside of the constricted channel 40. However, when the proximally-located sensor 44 is not compressed or moved towards the outer surface 38 of the introducer 14 but is instead elevated or spaced apart from the outer surface 38 of the introducer 14, an electrical contact or circuit may be open or broken, which the sensor 24 or controller 28 (FIG. 1) may correlate to the proximal portion 50 or the predetermined section 30 of the introducer 14 being located outside of the constricted channel 40.

Figure 6C:
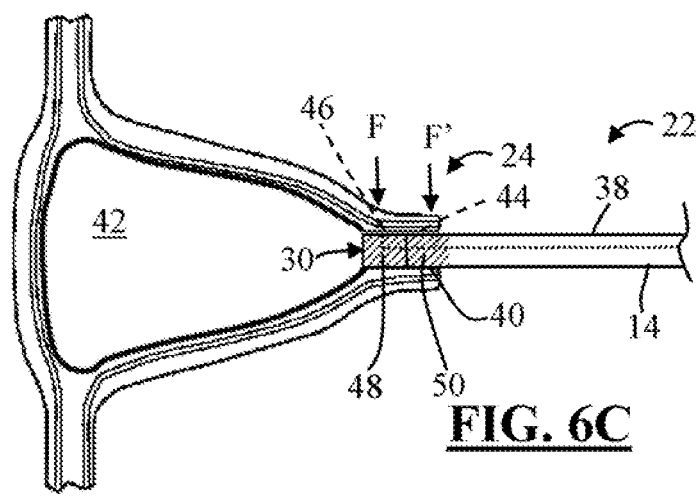

FIG. 6C illustrates the distal portion 22 of the introducer 14 moved or inserted further into the constricted channel 40. When the distal portion 22 of the introducer 14 is located inside the constricted channel 40, the intimate contact with the tissue of the constricted channel 40 causes a force F to remain applied onto the distally-located sensor 46, which causes the distal sensor 46 to remain compressed. A force F' is also onto the proximally-located sensor 44 due to the intimate contact of the tissue with the sensor 44, which causes the proximal sensor 44 to compress or deflect or be moved or biased towards the outer surface 38 of the introducer 14.

When both of the proximally-located and distally-located contact sections 44, 46 are compressed or moved towards the outer surface 38 of the introducer 14, an electrical contact or circuit may be completed, which the sensor 24 or controller 28 (FIG. 1) may correlate to both of the proximal and distal portions 48, 50 of the predetermined section 30 of the introducer 14 being located inside of the constricted channel 40.

Figure 6D:
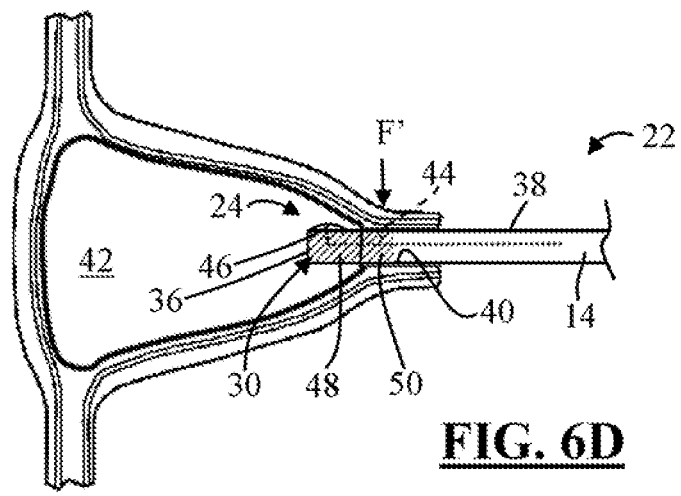

FIG. 6D illustrates the distal portion 22 of the introducer 14 moved or inserted further into the body lumen 42 such that the distal-most end 36 of the introducer 14 is located inside of the body cavity 42. When the distal portion 22 of the introducer 14 is located at least partially inside the body cavity 42 and partially inside the body lumen 40, the tissue of the body lumen 40 is no longer in intimate contact with the sensor 46 and thus no longer applies the pressure or force onto the distally-located sensor 46. Accordingly, the distally-located sensor 46 is not compressed or deflected or moved or biased towards the outer surface 38 of the introducer 14. Instead, the distally-located sensor 46 moves back into an elevated or spaced apart from the outer surface 38 of the introducer 14. However, the force F' remains on the proximally-located sensor 44, which causes the proximally-located sensor 44 to remain compressed or deflected or be moved or biased towards the outer surface 38 of the introducer 14.

When the distally-located sensor 46 is uncompressed or spaced apart from the outer surface 38 of the introducer 14, an electrical contact or circuit may be open or broken, which the sensor 24 or controller 26 (FIG. 1) may correlate to the distal portion 48 of the predetermined section 30 of the introducer 14 being located inside of the body cavity 42. When the proximally-located sensor 44 is compressed or moved towards the outer surface 38 of the introducer 14, an electrical contact or circuit may be closed or completed, which the sensor 24 and/or controller 28 (FIG. 1) may correlate to the proximal portion 50 of the predetermined section 30 of the introducer 14 being located inside of the body lumen 40.

Figure 6E:
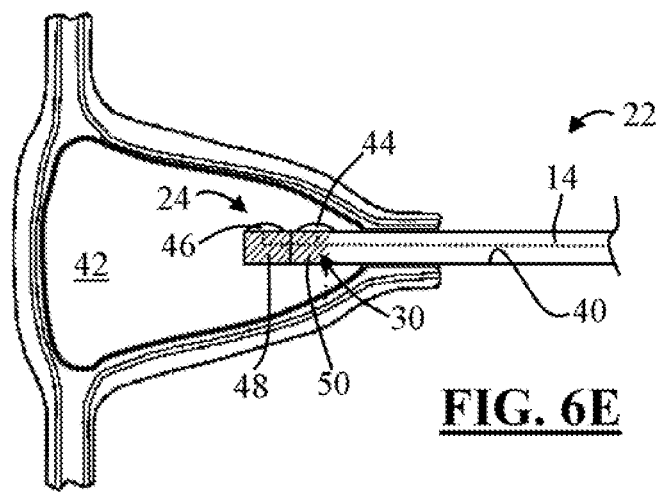

FIG. 6E illustrates the entire predetermined section 30 of the introducer 14 located inside of the body cavity 42. When the predetermined section 30 of the introducer 14 is located inside of the body cavity 42, the sensors 44, 46 are free of intimate contact with the tissue of the body lumen 40 and a force is no longer applied onto either of the sensors 44, 46. Instead, both of the proximal and distal sensors 44, 46 remain uncompressed, elevated, or spaced apart from the outer surface 38 of the introducer 14.

When the distally-located sensor 46 is uncompressed or spaced apart from the outer surface 38 of the introducer 14, an electrical contact or circuit may be open or broken, which the sensor 24 or controller 26 (FIG. 1) may correlate to the distal portion 48 of the predetermined section 30 of the introducer 14 being located inside of the body cavity 42. When the proximally-located sensor 44 is uncompressed or spaced apart from the outer surface 38 of the introducer 14, an electrical contact or circuit may be open or broken, which the sensor 24 or controller 26 (FIG. 1) may correlate to the proximal portion 50 of the predetermined section 30 of the introducer 14 being located inside of the body cavity 42.

By utilizing two (or more) sensors 48, 50, entry or movement of the introducer 14 into the body cavity 42 may be better controlled, especially since the length of the body lumen may vary. For example, after the sensor 24 or controller 28 determines that the distal portion 48 of the predetermined section 30 is located inside of the body cavity 42, treatment of the body cavity 42 may begin. For example, after the sensor 24 or controller 28 determines that the distal portion 48 of the predetermined section 30 is located inside of the body cavity 42 further movement of the introducer 14 into the body cavity 42 may cease or may continue at a slower speed to reduce risk of tissue perforation. For example, after the sensor 24 or controller 28 determines that the proximal portion 50 of the predetermined section 30 is located inside of the body cavity 42, treatment of the body cavity 42 may begin; a first treatment that occurs when only the distal portion 48 is located inside of the body cavity 42 may cease and another treatment of the body cavity 42 may begin after the proximal portion 50 is located inside of the body cavity 42.

While the afore-described example includes two sensors 44, 46 and two corresponding portions 48, 50, the predetermined section 30 may include more than two sensors and/or more than two portions. Insertion of the predetermined section may be controlled and/or understood by monitoring the sensors to reduce risk of tissue perforation, without having to use hysteroscopy and/or other feeler sensors or devices that contact tissue inside of the anatomy.

Figure 7:
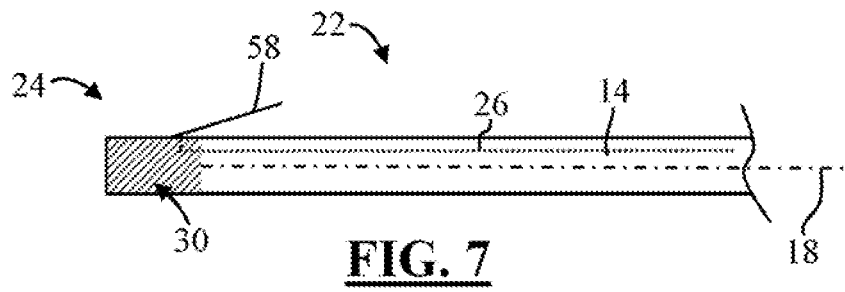
FIG. 7 is a side view of a distal portion of the medical device of FIG. 1.

FIG. 7 illustrates the distal portion 22 of the introducer 14. The introducer 14 comprises a predetermined section 30. The sensor 24 may be located within the predetermined section 30; the sensor 24 may be located distal of the predetermined section 30; or the sensor 24 may be located proximal of the predetermined section 30.

The sensor 24 includes an arm 58 that extends at an angle relative to the longitudinal axis 18 of the introducer 14. The arm 58 extends in a proximal direction, towards the hand piece 12 (FIG. 1). The sensor 24 illustrated in FIG. 7 may be used in combination with, or as a substitute for, any sensor disclosed herein.

The sensor in FIG. 7 is illustrated in a spaced-apart, uncompressed position, indicative of the predetermined section 30 being located outside of the constricted channel. This means that the predetermined section may be located inside of the body cavity or outside of both of the body cavity and the constricted channel and free of intimate contact with any tissue. The sensor 24 may be configured to supply one or more signals corresponding to the position of the sensor 24 to a controller for processing to alert or notify a user of the position of the predetermined section 30.

After the predetermined section 30 is located inside of a constricted channel, and the arm 58 of the sensor 24 is in intimate contact with tissue, a force applied onto the arm 58 causes the arm 58 to move or pivot into a compressed position, towards an outer surface of the introducer 14, in a clockwise direction. The sensor 24 may be configured to supply one or more signals corresponding to the position of the sensor 24 in the compressed position to a controller for processing to alert or notify a user of the position of the predetermined section 30 inside of the constricted channel.

Figure 8:
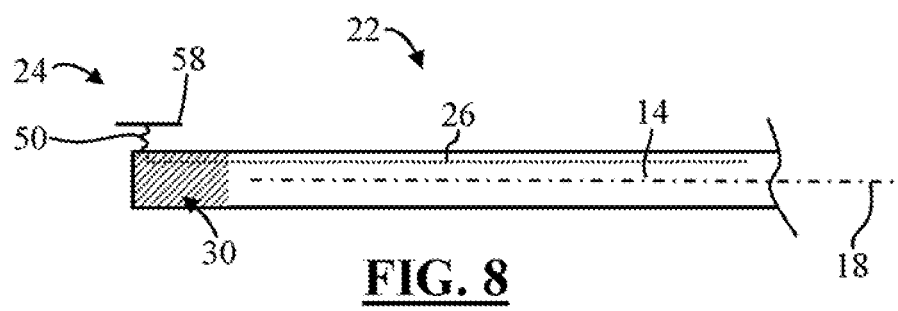
FIG. 8 is a side view of a distal portion of the medical device of FIG. 1.

In FIG. 8, the sensor 24 includes an arm 58 that extends generally parallel to the longitudinal axis 18 of the introducer 14. The sensor 24 includes a biasing member 52 located between the arm 58 and the outer surface 38 of the introducer 14 and may function to raise or move the arm 58 away from the introducer after a force is no longer acting on the arm 58 (i.e., when the sensor 24 and/or predetermined section is no longer positioned inside of a constricted channel. The sensor 24 and/or the biasing member 52 illustrated in FIG. 8 may be used in combination with, or a substitute for, any sensor disclosed herein.

The sensor in FIG. 8 is illustrated in a spaced-apart, uncompressed position, indicative of the predetermined section 30 being located outside of the constricted channel and free of intimate contact with tissue or anatomy. This means that the predetermined section may be located inside of the body cavity or outside of both of the body cavity and the constricted channel. The sensor 24 may be configured to supply one or more signals corresponding to the position of the sensor 24 to a controller for processing to alert or notify a user of the position of the predetermined section 30.

After the predetermined section 30 is located inside of a constricted channel, the sensor 24 or arm 58 may be in intimate contact with tissue, which applies a force applied onto the arm 58, causing the arm 58 to move or pivot into a compressed position, towards an outer surface of the introducer 14. The sensor 24 may be configured to supply one or more signals corresponding to the position of the sensor 24 in the compressed position to a controller for processing to alert or notify a user of the position of the predetermined section 30 inside of the constricted channel.

Figure 9:
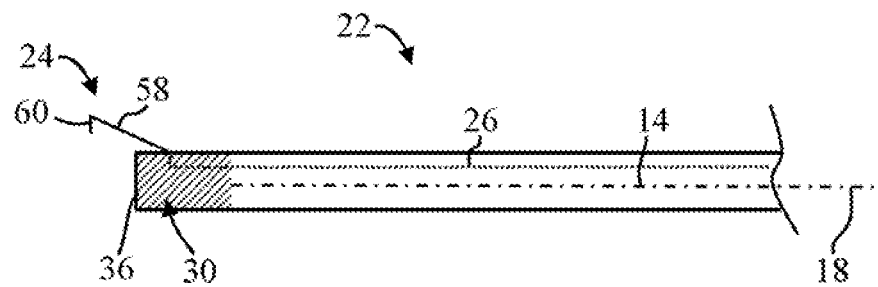
FIG. 9 is a side view of a distal portion of the medical device of FIG. 1.

In FIG. 9, the sensor 24 includes an arm 58 that extends in a distal direction and at an angle relative to the longitudinal axis 18 of the introducer 14. A distal end 60 of the arm 58 extends beyond a distal-most end 36 of the introducer 14 and/or a distal-most end 36 the predetermined section 30.

The sensor in FIG. 9 is illustrated in a spaced-apart, uncompressed position, indicative of the predetermined section 30 being located outside of the constricted channel and free of any intimate contact with tissue defining a body lumen or constricted channel. This means that the predetermined section may be located inside of the body cavity or outside of both of the body cavity and the constricted channel. The sensor 24 may be configured to supply one or more signals corresponding to the position of the sensor 24 to a controller for processing and to alert or notify a user of the position of the predetermined section 30.

After the predetermined section 30 is located inside of a constricted channel, the sensor 24 is in intimate contact with tissue defining a body lumen 40, which applies a force applied onto the arm 58, causing the arm 58 to move or pivot into a compressed position, towards an outer surface of the introducer 14, in a counter clockwise direction. The sensor 24 may then be configured to supply one or more signals corresponding to the position of the sensor 24 in the compressed position to a controller for processing to alert or notify a user of the position of the predetermined section 30 inside of the constricted channel.

Figure 10:
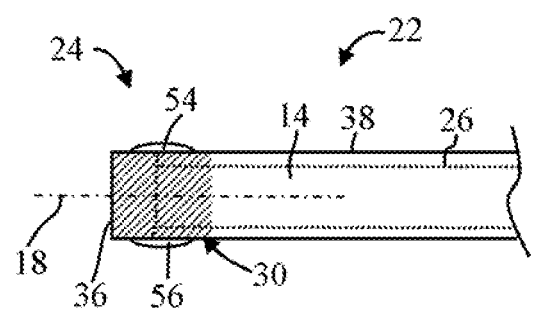
FIG. 10 is a side view of a distal portion of the medical device of FIG. 1.

FIG. 10 illustrates the distal portion 22 of the introducer 14. The introducer 14 comprises a predetermined section 30. The sensor 24 comprises a first sensor 54 and a second sensor 56. The sensors 54, 56 are provided at opposing sides of the introducer 14. For example, when looking at a front view of the introducer 14, sensor 54 may be located at a 12 o'clock position and sensor 56 may be located at a 6 o'clock position. The sensors 54, 56 are illustrated in an uncompressed or steady state position. After the predetermined section 30 is located inside of a constricted channel 40, the sensor 24 is in intimate contact with tissue of the constricted channel 40, which causes a force to be applied onto the sensors 54, 56. The force may cause the sensors 54. 56 to move or compress towards an outer surface 38 of the introducer 14. As was discussed above in the other examples, a signal may be generated by the sensors 54, 56 after the sensors 54, 56 are compressed and then communicated to a controller or user indicative of the predetermined section 30 being located inside of the constricted channel 40.

After a force is no longer applied onto the sensors 54, 56 which may occur when the sensors 54, 56 are free of any intimate contact with tissue, the sensors 54, 56 may be configured to move away from the outer surface 38 of the introducer 14 back into a steady state position. As was also discussed above in the other examples above, a signal may be generated after the sensors 54, 56 uncompressed and then communicated to a controller 28 or user indicative of the predetermined section 30 no longer being located inside of the constricted channel and instead located inside of a body cavity 42 or outside of both the body cavity 42 and the constricted channel.

Figure 11:
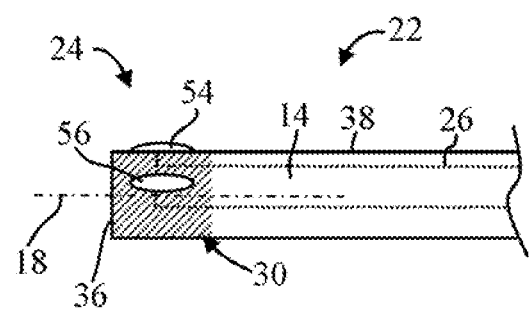
FIG. 11 is a side view of a distal portion of the medical device of FIG. 1.

FIG. 11 illustrates the distal portion 22 of the introducer 14. The introducer 14 comprises a predetermined section 30. The sensor 24 comprises a first sensor 54 and a second sensor 56. The sensors 54, 56 are located adjacent one another, rather than spaced apart on opposite sides of the introducer 14 in FIG. 10. The function of the sensors 54, 56 is substantially similar to the description above at FIG. 10, therefore in the interest of brevity it will not be repeated again.

Figure 12:
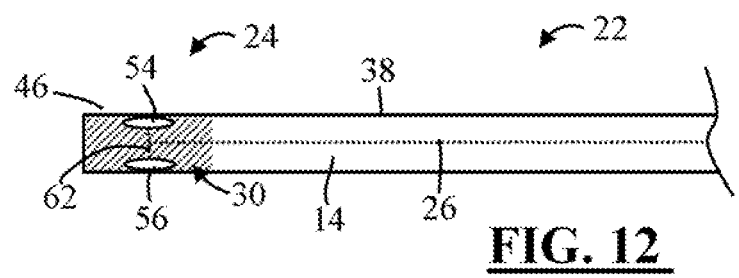
FIG. 12 is a side view of a distal portion of the medical device of FIG. 1.

FIG. 12 illustrates an introducer with a sensor 24 comprising a first sensor 54 and a second sensor 56. The sensors 54, 56 may extend beyond or may be proud of the outer surface 38 of the introducer 14. Or the sensors 54, 56 may be flush or sub-flush with the outer surface 38 of the introducer 14.

The sensors 54, 56 may be electrical terminals that are electrically connected together via conductor 62 to have an open circuit between them. The sensor 24 is in electrical communication with a controller 28 (FIG. 1) via communication device 26.

Figure 13:
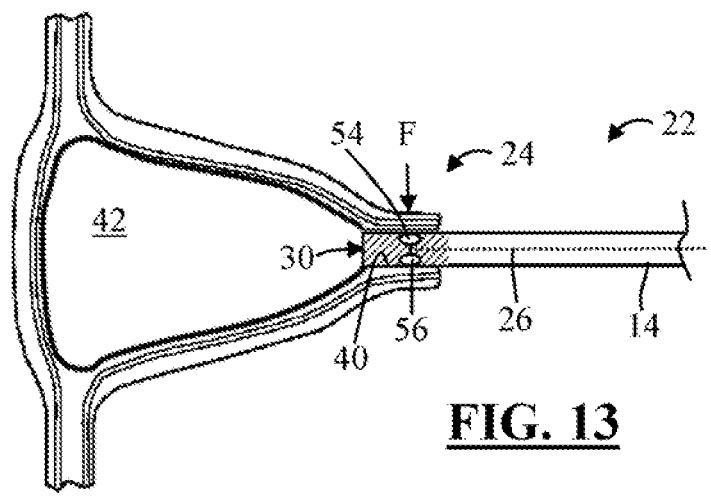
FIG. 13 is a side view of a distal portion of the medical device of FIG. 12 positioned inside of a constricted channel.

Referring now to FIG. 13, after the introducer 14 and/or predetermined section 30 is located inside of a constricted channel 40, the sensors 54, 56 are in intimate contact with tissue or anatomy defining the constricted channel 40, which completes the electrical circuit between the sensors 54, 56 through the conductive tissue. A signal is then generated and provided by the controller 28 indicative of the closed circuit, which is indicative that both sensors 54, 56 or terminals are in contact with the tissue, which means the predetermined section 30 is located inside of the constricted channel 40.

After the introducer is removed from the constricted channel 30, the tissue of the constricted channel is no longer in contact or free of intimate contact with the sensors 54, 56 or terminals causing the circuit between the sensors 54, 56 or terminals to be open so that a signal is not generated. The controller 28 may then be configured to generate a signal to a user or computer notifying or alerting that the predetermined section 30 is no longer located within the constricted channel 40 and is instead located either in the body cavity 42 or outside of both the body cavity 42 and the constricted channel 40.

It is understood that one or more of the sensors 24 from any of the FIGS. herein may be combined, omitted, and/or duplicated with each other. In other words, for example, a sensor 24 from FIG. 2 may be duplicated, added, or substituted for one or more of the sensors 24 disclosed in one or more of FIGS. 4-13, and vice versa.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device comprising:
an introducer configured to be inserted into a uterine cavity through a cervical canal which is narrower than the uterine cavity, the introducer extending from a proximal end to a distal end and comprising a treatment device and a predetermined section at the distal end, the distal end of the introducer being contoured or tapered to assist in inserting the introducer through the cervical canal and into the uterine cavity while preventing perforation of surrounding tissue, the treatment device configured to activate a treatment modality at the distal end of the introducer;
a sensor located at the predetermined section; and
a controller;
wherein, in use:
the sensor generates a first status signal while the predetermined section of the introducer is located inside of the cervical canal and the sensor is in intimate contact with tissue of the cervical canal;
the sensor generates a second status signal while the predetermined section of the introducer is located inside of an area that is wider than the cervical canal and the sensor is free of the intimate contact with the tissue;
the controller generates a signal which indicates the sensor is free of the intimate contact with the tissue and the predetermined section of the introducer is located in the uterine cavity when the second status signal is preceded by the first status signal;
the treatment device activates the treatment modality at the distal end of the introducer after determining that the predetermined section of the introducer is located in the uterine cavity; and
the controller does not generate the signal which indicates the sensor is free of the intimate contact with the tissue and the predetermined section of the introducer is located in the uterine cavity when the second status signal is not preceded by the first status signal.

2. The medical device according to claim 1, wherein while the predetermined section of the introducer is located inside of the cervical canal and the sensor is in intimate contact with the tissue of the cervical canal, contact with the tissue applies a force onto the sensor to move a portion of the sensor towards an outer surface of the introducer and into a compressed position, and
wherein the sensor is configured to correlate movement of the sensor towards the outer surface of the introducer or the sensor being in the compressed position as the predetermined section of the introducer being located inside of the cervical canal.

3. The medical device according to claim 2, wherein while the predetermined section of the introducer is located inside of the uterine cavity, the sensor is free of the intimate contact with the tissue and the sensor moves away from the outer surface of the introducer into an elevated position,
wherein the sensor is configured to correlate movement of the sensor away from the outer surface of the introducer or the sensor being in the elevated position as the predetermined section of the introducer being located inside of the uterine cavity.

4. The medical device according to claim 1, wherein the sensor rotates relative to the predetermined section.

5. The medical device according to claim 1, wherein the sensor displaces relative to the predetermined section.

6. The medical device according to claim 1, wherein the sensor comprises a distally-located contact sensor and a proximally-located contact sensor, and wherein the sensor is configured to correlate a lack of intimate contact of tissue on the distally-located contact sensor and intimate contact of tissue on the proximally-located contact sensor as the predetermined section of the introducer being at least partially located inside of the cervical canal.

7. The medical device according to claim 1, wherein the sensor comprises a distally-located contact sensor and a proximally-located contact sensor, and wherein the sensor is configured to correlate a lack of intimate contact of tissue on the distally-located contact sensor and a lack of intimate contact of tissue on the proximally-located contact sensor as the predetermined section of the introducer being located inside of the uterine cavity.

8. The medical device according to claim 1, wherein the sensor comprises a distally-located contact sensor and a proximally-located contact sensor, and wherein the sensor is configured to correlate intimate contact of tissue on the distally-located contact sensor and intimate contact of tissue on the proximally-located contact sensor as the predetermined section of the introducer being located inside of the cervical canal.

9. The medical device according to claim 1, wherein the sensor comprises a distally-located contact sensor and a proximally-located contact sensor, and wherein the sensor is configured to correlate intimate contact with tissue on the distally-located contact sensor and lack of intimate contact with tissue on the proximally-located contact sensor as the predetermined section of the introducer being partially located inside of the cervical canal.

10. The medical device according to claim 1, wherein, in use:
the controller generates a second signal which indicates the predetermined section of the introducer is located in the cervical canal when the sensor generates the first status signal.

11. The medical device according to claim 1, wherein the first status signal is indicative of the sensor being in a compressed position.

12. The medical device according to claim 11, wherein the second status signal is indicative of the sensor being in an uncompressed position.

13. The medical device according to claim 1, wherein the first status signal is indicative of physical contact between the sensor and the cervical canal.

14. The medical device according to claim 13, wherein the second status signal is indicative of the absence of contact between the sensor and the cervical canal.

15. A medical device comprising:
an introducer configured to be inserted into a uterine cavity through a cervical canal which is narrower than the uterine cavity, the introducer including a treatment device configured to activate a treatment modality at a distal end of the introducer;
a sensor at the distal end of the introducer; and
a controller;
wherein the introducer is configured to place the sensor in intimate contact with tissue during insertion of the introducer into the cervical canal and to remove the sensor from the intimate contact with tissue after the introducer is inserted into the uterine cavity;
wherein, in use:
the sensor provides a first status signal when the sensor is in intimate contact with the tissue inside of the cervical canal and provides a second status signal when the sensor is free of the intimate contact with the tissue;
the controller generates a signal which indicates the distal end of the introducer is located in the uterine cavity when the second status signal is preceded by the first status signal;
the treatment device activates the treatment modality at the distal end of the introducer after determining that the distal end of the introducer is located in the uterine cavity; and
the controller does not generate the signal which indicates the distal end of the introducer is located in the uterine cavity when the second status signal is not preceded by the first status signal.

16. The medical device according to claim 15, wherein the sensor comprises a proximally-located contact sensor and a distally-located contact sensor, and wherein the sensor is configured to provide the first status signal after the distally-located contact sensor is in the intimate contact with the tissue and the proximally-located contact sensor is in the intimate contact with the tissue.

17. The medical device according to claim 15, wherein the sensor comprises a proximally-located contact sensor and a distally-located contact sensor, and wherein the sensor is configured to provide the second status signal after the distally-located contact sensor is free of the intimate contact with the tissue and the proximally-located contact sensor is free of the intimate contact with the tissue.

18. The medical device according to claim 15, wherein the first status signal is indicative of the sensor being in a compressed position.

19. The medical device according to claim 18, wherein the second status signal is indicative of the sensor being in an uncompressed position.

20. A medical device comprising:
an introducer configured to be inserted into a uterine cavity through a cervical canal which is narrower than the uterine cavity, the introducer extending from a proximal end to a distal end and comprising a distal section at the distal end, the distal end of the introducer being contoured or tapered to assist in inserting the introducer through the cervical canal and into the uterine cavity while preventing perforation of surrounding tissue, the introducer further comprising a treatment device configured to activate a treatment modality at the distal end of the introducer;
a sensor located at the distal section; and
a controller;
wherein, in use:
the sensor generates a first status signal while the distal section of the introducer is located inside of the cervical canal and the sensor is in intimate contact with tissue;
the sensor generates a second status signal while the distal section of the introducer is located inside of an area that is wider than the cervical canal and the sensor is free of the intimate contact with the tissue;
the controller generates a signal which indicates the distal section of the introducer is located in the uterine cavity when the second status signal is preceded by the first status signal;
the treatment device activates the treatment modality at the distal end of the introducer after determining that the distal section of the introducer is located in the uterine cavity; and
the controller does not generate the signal which indicates the distal section of the introducer is located in the uterine cavity when the second status signal is not preceded by the first status signal.

* * * * *